(12) United States Patent
Palti

(10) Patent No.: US 8,718,756 B2
(45) Date of Patent: *May 6, 2014

(54) OPTIMIZING CHARACTERISTICS OF AN ELECTRIC FIELD TO INCREASE THE FIELD'S EFFECT ON PROLIFERATING CELLS

(75) Inventor: Yoram Palti, Haifa (IL)

(73) Assignee: Novocure Limited, St. Helier (JE)

( * ) Notice: Subject to any disclaimer, the term of this patent is extended or adjusted under 35 U.S.C. 154(b) by 784 days.

This patent is subject to a terminal disclaimer.

(21) Appl. No.: 12/851,761

(22) Filed: Aug. 6, 2010

(65) Prior Publication Data

US 2010/0324547 A1 Dec. 23, 2010

Related U.S. Application Data

(63) Continuation of application No. 11/537,026, filed on Sep. 29, 2006, now Pat. No. 7,917,227.

(60) Provisional application No. 60/723,560, filed on Oct. 3, 2005.

(51) Int. Cl.
*A61N 1/00* (2006.01)

(52) U.S. Cl.
USPC .............................................. 607/2; 607/66

(58) Field of Classification Search
USPC ................................................ 607/2, 65–76
See application file for complete search history.

(56) References Cited

U.S. PATENT DOCUMENTS

| | | |
|---|---|---|
| 2,220,269 A | 11/1940 | Patzold et al. |
| 3,991,770 A | 11/1976 | LeVeen |
| 4,016,886 A | 4/1977 | Doss et al. |
| 4,121,592 A | 10/1978 | Whalley |
| 4,263,920 A | 4/1981 | Tasto et al. |
| 4,467,809 A | 8/1984 | Brighton |
| 4,472,506 A | 9/1984 | Liburdy |
| 4,622,952 A | 11/1986 | Gordon |
| 4,626,506 A | 12/1986 | Zimnermann et al. |
| 4,676,258 A | 6/1987 | Inokuchi et al. |
| 4,822,470 A | 4/1989 | Chang |
| 4,846,178 A | 7/1989 | Fuxue et al. |
| 4,846,196 A | 7/1989 | Wiksell et al. |

(Continued)

FOREIGN PATENT DOCUMENTS

| | | |
|---|---|---|
| EP | 0330797 | 9/1989 |
| GB | 1419660 | 12/1975 |

(Continued)

OTHER PUBLICATIONS

Hofmann et al., "Electronic Genetic-Physical and Biological Aspects of Cellular Electomanipulation", IEEE Eng. in Med. and Biology Mag., Dec. 1986, p. 6-23, New York.

(Continued)

*Primary Examiner* — Scott Getzow
(74) *Attorney, Agent, or Firm* — Proskauer

(57) ABSTRACT

AC electric fields at particular frequencies and field strengths have been shown to be effective for destroying rapidly proliferating cells such as cancer cells. The effectiveness of such fields is improved when the field is sequentially switched between two or more different directions. The effectiveness of such fields can be improved even further by choosing the rate at which the field is switched between the various directions.

13 Claims, 6 Drawing Sheets

(56) References Cited

U.S. PATENT DOCUMENTS

| | | |
|---|---|---|
| 4,923,814 A | 5/1990 | Marshall |
| 4,936,303 A | 6/1990 | Detwiler et al. |
| 4,971,991 A | 11/1990 | Umemura et al. |
| 5,099,756 A | 3/1992 | Franconi et al. |
| 5,158,071 A | 10/1992 | Umemura et al. |
| 5,236,410 A | 8/1993 | Granov et al. |
| 5,269,304 A | 12/1993 | Matthews |
| 5,312,813 A | 5/1994 | Costerton et al. |
| 5,386,837 A | 2/1995 | Sterzer |
| 5,389,069 A | 2/1995 | Weaver |
| 5,441,532 A | 8/1995 | Fenn |
| 5,441,746 A | 8/1995 | Chagnon |
| 5,468,223 A | 11/1995 | Mir |
| 5,549,656 A | 8/1996 | Reiss |
| 5,606,971 A | 3/1997 | Sarvazyn |
| 5,674,267 A | 10/1997 | Mir et al. |
| 5,718,246 A | 2/1998 | Vona |
| 5,807,257 A | 9/1998 | Bridges |
| 5,891,182 A | 4/1999 | Fleming |
| 5,964,726 A | 10/1999 | Korenstein et al. |
| 5,976,092 A | 11/1999 | Chinn |
| 5,984,882 A | 11/1999 | Rosenschein et al. |
| 6,027,488 A | 2/2000 | Hofmann et al. |
| 6,043,066 A | 3/2000 | Mangano et al. |
| 6,055,453 A | 4/2000 | Hofmann et al. |
| 6,068,650 A | 5/2000 | Hofmann et al. |
| 6,096,020 A | 8/2000 | Hofmann et al. |
| 6,319,901 B1 | 11/2001 | Bernard et al. |
| 6,366,808 B1 | 4/2002 | Schroeppel et al. |
| 6,413,255 B1 | 7/2002 | Stern |
| 6,447,499 B2 | 9/2002 | Gray |
| 6,856,839 B2 | 2/2005 | Litovitz |
| 6,868,289 B2 | 3/2005 | Palti |
| 7,016,725 B2 | 3/2006 | Palti |
| 7,089,054 B2 | 8/2006 | Palti |
| 7,136,699 B2 | 11/2006 | Palti |
| 7,146,210 B2 | 12/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,917,227 B2 * | 3/2011 | Palti ............................ 607/66 |
| 2002/0193832 A1 | 12/2002 | Gray |
| 2002/0193833 A1 | 12/2002 | Dimmer et al. |
| 2003/0060856 A1 | 3/2003 | Chornenky et al. |
| 2003/0191506 A1 | 10/2003 | Shloznilov |
| 2004/0068296 A1 | 4/2004 | Palti |
| 2004/0068297 A1 * | 4/2004 | Palti ............................ 607/2 |
| 2005/0209640 A1 | 9/2005 | Palti |
| 2005/0209641 A1 | 9/2005 | Palti |
| 2005/0240173 A1 | 10/2005 | Palti |
| 2005/0240228 A1 | 10/2005 | Palti |
| 2006/0149341 A1 | 7/2006 | Palti |
| 2006/0233867 A1 | 10/2006 | Palti |
| 2006/0241547 A1 | 10/2006 | Palti |
| 2006/0276858 A1 | 12/2006 | Palti |
| 2006/0282122 A1 | 12/2006 | Palti |
| 2007/0033660 A1 | 2/2007 | Palti |
| 2007/0184020 A1 | 8/2007 | Kalbe et al. |
| 2007/0225766 A1 | 9/2007 | Palti |
| 2007/0239213 A1 | 10/2007 | Palti |
| 2008/0221630 A1 | 9/2008 | Palti |
| 2008/0319372 A1 | 12/2008 | Palti |
| 2009/0043346 A1 | 2/2009 | Palti |
| 2009/0076366 A1 | 3/2009 | Palti |

FOREIGN PATENT DOCUMENTS

| | | |
|---|---|---|
| GB | 2026322 | 2/1980 |
| GB | 2043453 | 10/1980 |
| WO | 0160994 | 8/2001 |

OTHER PUBLICATIONS

Berg et al., "Electric Field Effects on Bilogical Membranes:Electoincorporation and Electofusion",Ettore Maj Inter. Science, 1987,p. 135-166,vol. 32,Phys. Science, New York.

Kirson et al., "Disruption of Cancer Cell Replication by Alternating Electric Fields", Cancer Research 64, May 2004, p. 3288-3295, Haifa, Israel.

Asbury et al., "Trapping of DNA in Nonuniform Oscillating Electric Fields", Biophysical Journal, Feb. 1998, p. 1024-1030, vol. 74,Seattle, WA.

Janigro et al., "Alternating current electrical stimulation enhanced chemotherapy: a novel strategy to bypass multidrug resistance in tumor cells", BMC Cancer, 2006, 6:72.

Giladi et al., Microbial Growth Inhibition by Alternating Electric Fields, Antimicrobial Agents and Chemotherapy, Oct. 2008, p. 3517-3522.

Search Report and Written Opinion from corresponding application PCT/US2008/002134, Feb. 19, 2008.

* cited by examiner

OPTIMIZING CHARACTERISTICS OF AN ELECTRIC FIELD TO INCREASE THE FIELD'S EFFECT ON PROLIFERATING CELLS

CROSS REFERENCE TO RELATED APPLICATIONS

This application is a continuation of application 11/537,026, filed Sep. 29, 2006, which claims the benefit of U.S. provisional application No. 60/723,560, filed Oct. 3, 2005. Each of the above-identified applications is incorporated herein by reference.

BACKGROUND

U.S. Pat. Nos. 6,868,289 and 7,016,725, each of which is incorporated herein by reference, disclose methods and apparatuses for treating tumors using AC electric fields in the range of 1-10V/cm, at frequencies between 50 kHz and 500 kHz, and that the effectiveness of those fields is increased when more than one field direction is used (e.g., when the field is switched between two or three directions that are oriented about 90° apart from each other). Those alternating electric fields are referred to herein as Tumor Treating Fields, or TTFields.

SUMMARY OF THE INVENTION

The effectiveness of TTFields in stopping the proliferation of and destroying living cells that proliferate rapidly (e.g., cancer cells) can be enhanced by choosing the rate at which the field is switched between the various directions.

DETAILED DESCRIPTION OF THE PREFERRED EMBODIMENTS

Since electric fields sum as vectors, two or more fields with different directions cannot be applied simultaneously at a given location. Instead, the different field directions must be applied sequentially, by applying a first field in one direction for a certain period of time t1, and then applying a second field in another direction for a period t2. During t2 the first field is not active and during t1 the second field is inactive. When this cycle is repeated over and over, the result is that sequential field pulses of changing directions are applied in a cyclic manner.

Figure 1:
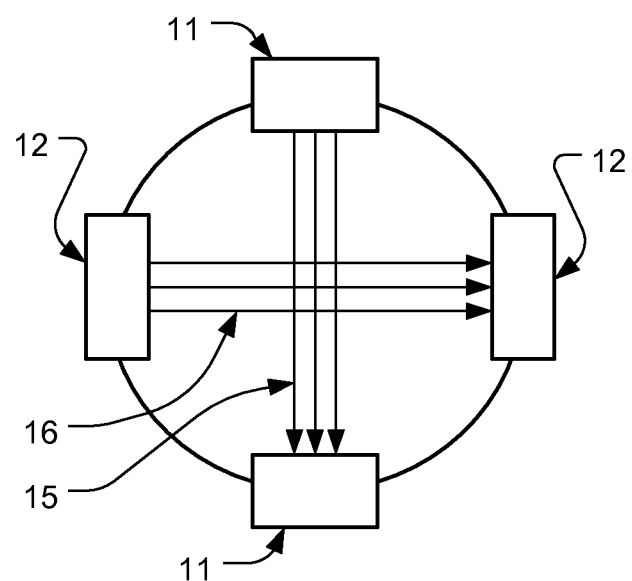
FIG. 1 is a schematic representation of two pairs of insulated electrodes that alternately apply TTFields to target region.

The inventor has determined that that the effectiveness of TTFields for destroying proliferating cells in tissue culture as well as malignant tumors in experimental animals is dependent on the rate of switching between the various directions of which the fields are applied. In a set of experiments, TTFields were applied to the tissue cultures or experimental animals by means of two pairs 11, 12 of insulated electrodes that alternately apply TTFields 15, 16 normal to each other, shown schematically in FIG. 1. The waveforms applied were 100-200 kHz alternating fields modulated to stay On and Off for half cycle durations ranging from 10 ms to 1000 ms.

Figure 2:
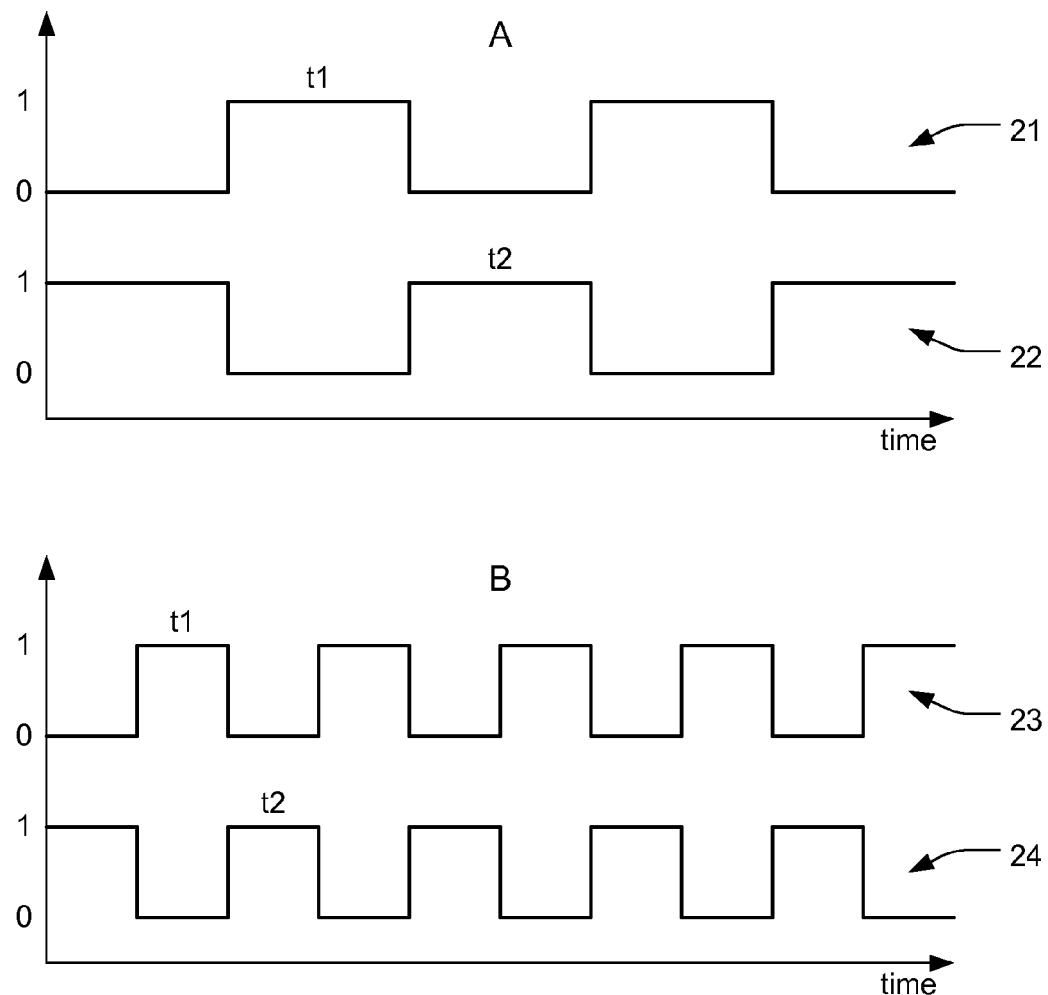
FIG. 2 shows examples of waveforms that are suitable for switching the fields that are applied between the electrodes on and off.

FIG. 2 shows two examples of waveforms that are suitable for modulating the AC signals that were applied between the electrodes: a first pair A of 50% duty cycle waveforms 21, 22 time shifted with respect to each other such that one is on when the other is off, and a second pair B of 50% duty cycle waveforms 23, 24 that is similar to the first set of waveforms, but switched at twice the frequency. Note that each set of waveforms consists of two 50% duty cycle square waves that are shifted in phase by one half cycle with respect to each other.

Figure 3:
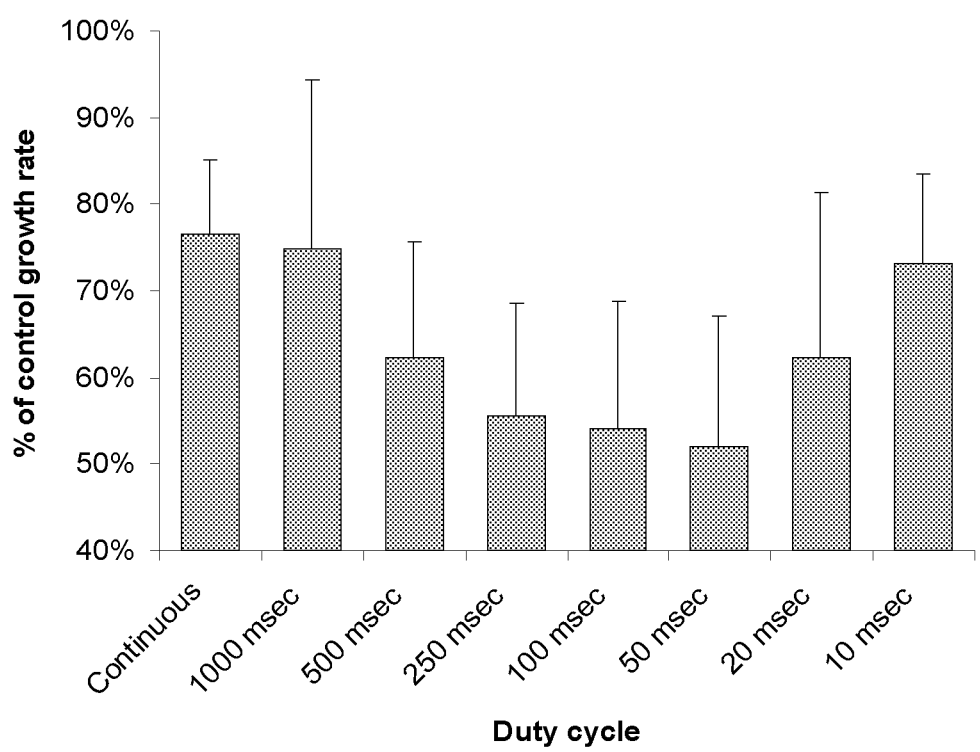
FIG. 3 depicts the changes in growth rate of a glioma cell culture treated with alternating electric fields switched between two directions at different switching rates.

FIG. 3 depicts the results of one set of experiments by plotting the changes in growth rate of a glioma cell culture (F98) treated with 200 kHz alternating electric field waveforms switched between two directions at different switching rates. Experimental data was also obtained for the case where the field was applied continuously in one direction only. (Note that the control baseline of 100% is for the case when no field was applied.) The data shows that some switching frequencies are more effective than others for reducing the proliferation of glioma tumor cells in culture. The highest effectiveness was found when the half cycle duration was 50 ms (with a similar Off duration) waveform. However, the effectiveness differences in the range of 250 ms to 50 ms were small. Within this range, the cell proliferation rate is reduced to about half of what it is when either a continuous field was applied, or when a 1000 ms half cycle duration waveform is used.

Figure 4:
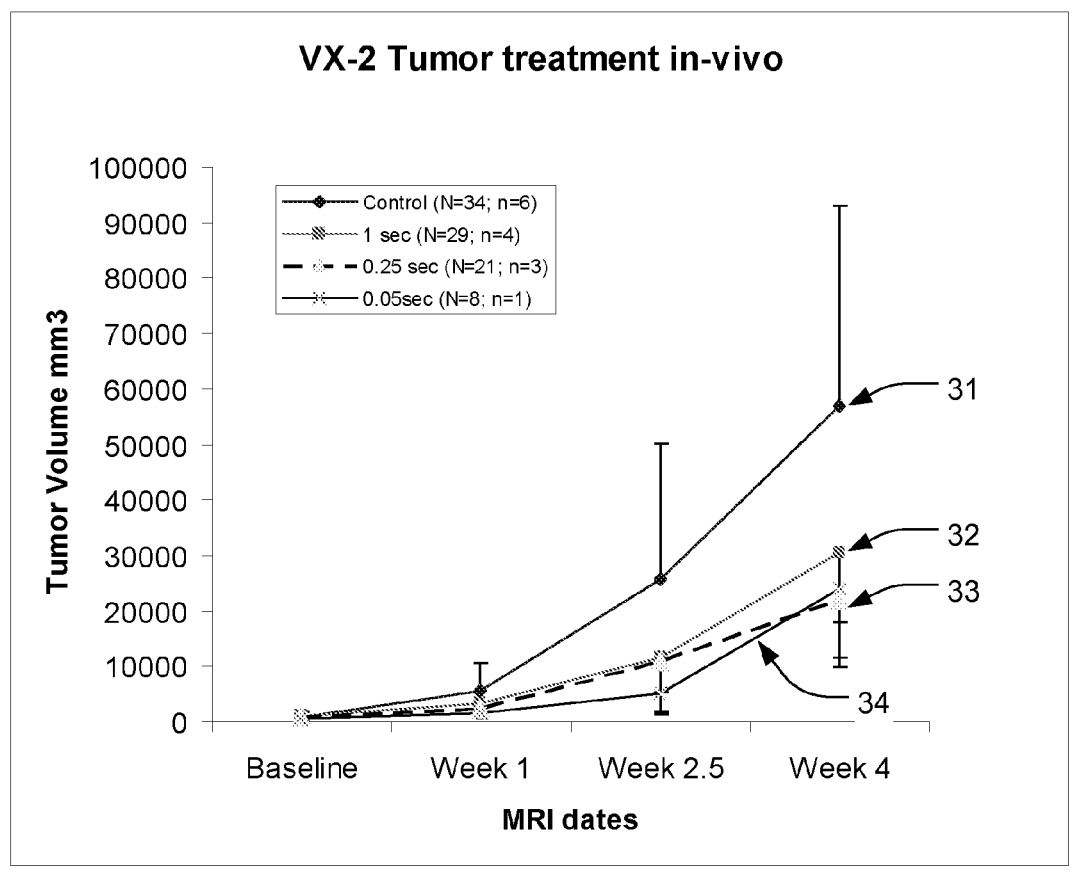
FIG. 4 is a graph of tumor volume vs. time for fields that were switched between two directions at different switching rates.

FIG. 4 is a graph of tumor volume vs. time for a set of experiment, and it shows the effect of 200 kHz TTFields on Vx2 carcinoma growth in vivo, when the fields were applied in two different directions at different switching rates. In the experiment, tumors from the carcinoma line Vx2 were inoculated under the kidney capsule in rabbits. As expected, the tumor size increases with time during the 4 week follow up period in the control, non-treated, group of rabbits (curve 31). The growth rate was slower when the fields were applied in different directions with a switch in direction every 1000 ms (curve 32); and the growth rate was even slower when the field's direction was switched every 250 ms (curve 33) or every 50 ms (curve 34). Thus, we see that the effectiveness of the treatment is significantly higher for waveform having half duty cycle durations of between 50 and 250 ms, as compared with 1000 ms half cycles.

Based on the above, the following approach is recommended for tumor treatment with TTFields: Treatment should be carried out with at least two field directions, such that each pair of electrodes is activated for On periods of a duration that is preferably between 50 and 250 ms, interposed by Off periods of a similar duration. The TTFields basic alternation frequency (which corresponds to the carrier frequency in an amplitude modulation system) should preferably be in the range of 50-500 kHz, and more preferably in the range of 100-200 kHz. The field intensity is preferably at least 1 V/cm, and more preferably between 1 and 10 V/cm.

Figure 5:
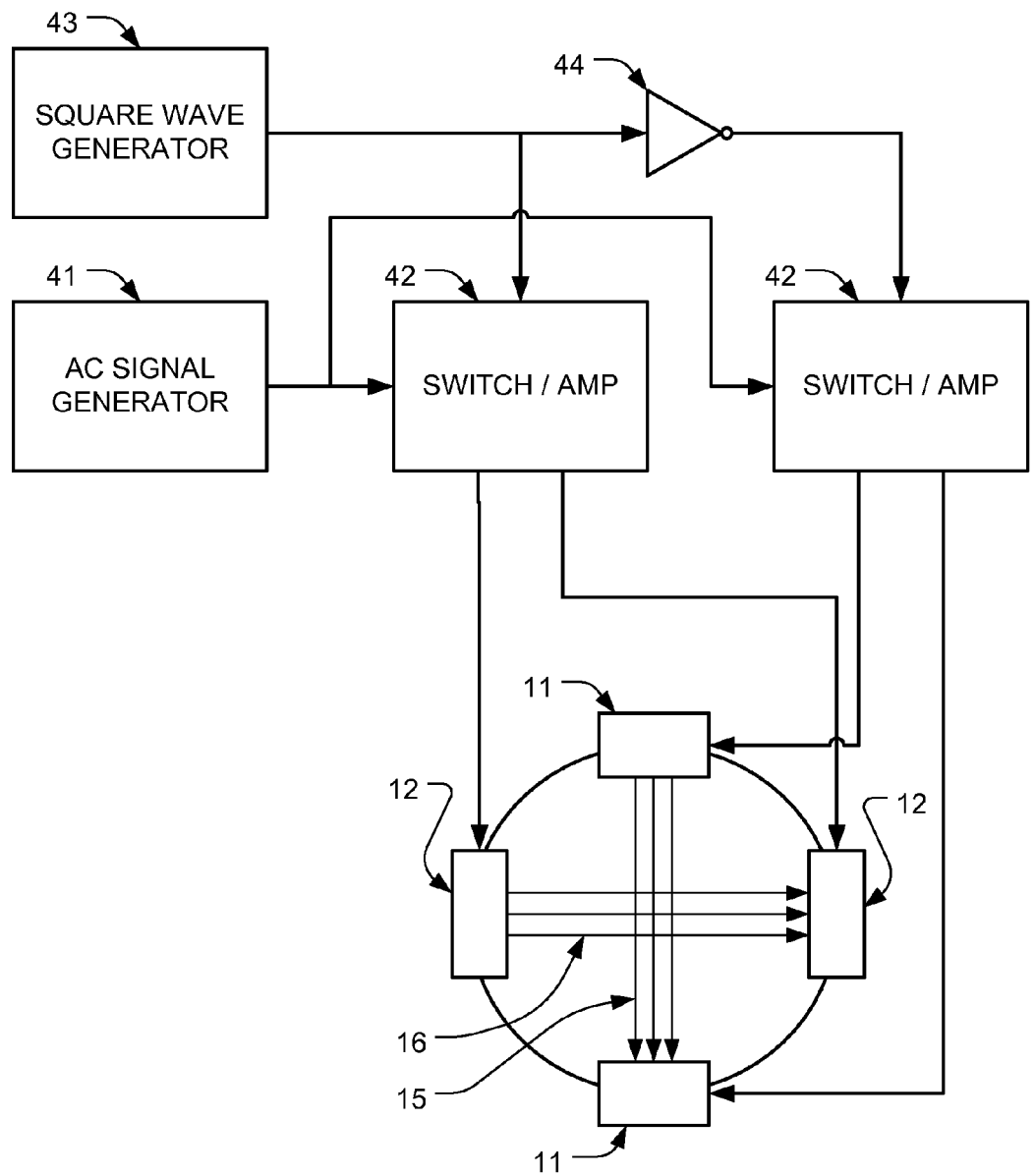
FIG. 5 is a block diagram of a system for generating the TTFields in different directions.

FIG. 5 is a block diagram of a system for generating the TTFields in different directions by driving a first electrode pair 11 and a second electrode pair 12 that are positioned about a target. An AC signal generator 41 generates a sinusoid, preferably between 100-200 kHz, and a square wave generator 43 generates a square wave that resembles the wave 21 shown in FIG. 2. Preferably the output of the square wave is high between 50 and 250 ms and low for an equal amount of time in every cycle, although duty cycles that deviate from 50% may also be used. An inverter 44 inverts this square wave, thereby providing the second wave 22 shown in FIG. 2. The amplifiers 42 amplify the sinusoid when their control input is in one state, and shut off when their control input is in the other state. Since the control input for the two amplifiers are out of phase, the amplifiers will alternately drive either the first electrode pair 11 or the second electrode pair 12 to generate either the first field 15 or the second field 16 in the target region. Of course, persons skilled in the relevant arts will recognize that a wide variety of other circuits may be used to alternately drive either the first or second pair of electrodes. For example, a suitable switching circuit may provided to route the output of a single amplifier to either the first or second pair of electrodes in an alternating manner, with the switching controlled by a single square wave.

Figure 6:
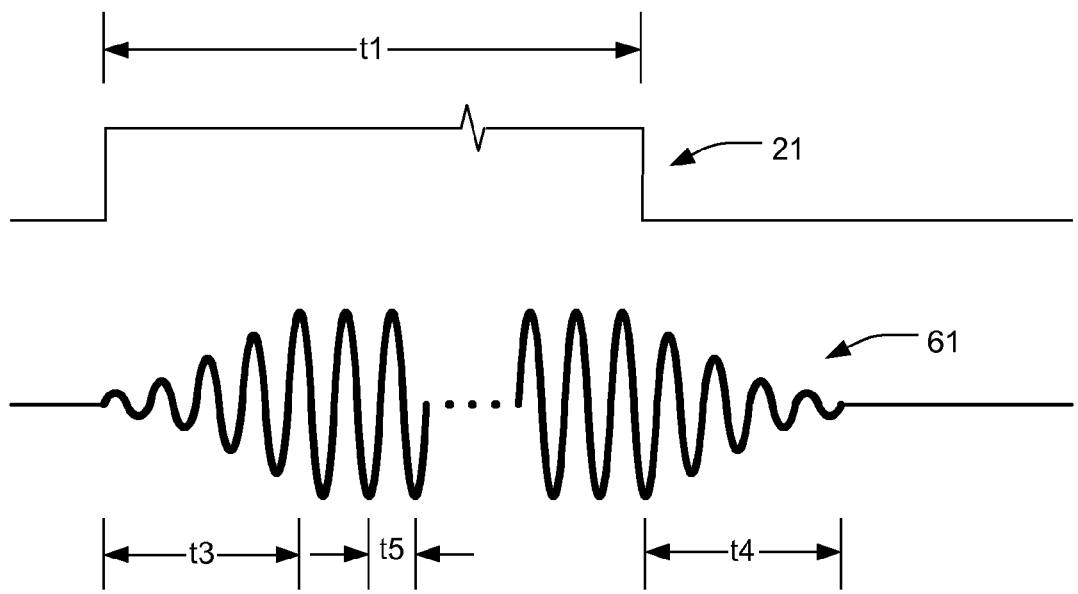
FIG. 6 illustrates a preferred waveform for driving the electrodes.

As explained in U.S. Pat. No. 6,868,289, insulated electrodes are preferred for in vivo applications. Preferably, care should be taken to avoid overheating of the tissues by the capacitive currents and dielectric losses in the insulated electrodes. It is also preferable to avoid the generation of spikes during the switching process. This can be done, for example, by carrying out the switching itself while the AC signal is turned off and immediately afterwards turning the signal on. The rate of turning the field on t3 and off t4 should preferably be done at a rate that is slow relative to the reciprocal of the field frequency (i.e., the period t5), and fast relative to the half cycle duration tl, t2, as seen in FIG. 6 for waveform 61. An example of a suitable turn-on rate t3 and turn-on rate t4 is to reach 90% of the steady-state values within about 1-5 ms. Circuitry for implementing this slow turn on may be implemented using a variety of approaches that will be apparent to persons skilled in the relevant arts, such as using a slow-rising control signal to drive an accurate AM modulator, or by driving a gain control of the amplifier with a square wave and interposing a low pass filter in series with the gain control input.

While examples of the invention are described above in the context of F98 glioma and Vx2 carcinoma, the switching rate may be optimized for other cancers or other rapidly proliferating cells by running experiments to determine the best switching rate, and subsequently using that switching rate to treat the problem in future cases.

I claim:

1. An apparatus for applying a therapeutic electric field to a target region, the apparatus comprising:

a first pair of insulated electrodes, each electrode having a conductor and a surface configured for placement against a patient's body that is insulated from the conductor;

a second pair of insulated electrodes, each electrode having a conductor and a surface configured for placement against a patient's body that is insulated from the conductor;

a signal generator that generates a periodic control signal with first and second output states, the first and second output states each having a duration between 20 and 500 ms;

an AC signal generator that generates a first AC signal across the conductors of the first pair of electrodes when the control signal is in the first output state and generates a second AC signal across the conductors of the second pair of electrodes when the control signal is in the second output state, the first and second AC signals having a frequency between 50 and 500 kHz.

2. The apparatus of claim 1, wherein the duration of the first output state is between 50 and 250 ms, and the duration of the second output state is between 50 and 250 ms.

3. The apparatus of claim 2, wherein the first and second AC signals having a frequency between 100 and 200 kHz.

4. The apparatus of claim 1, wherein the AC signal generator comprises a single signal source and a switch that distributes an output of the single signal source to either the first pair of electrodes or the second pair of electrodes.

5. The apparatus of claim 1, wherein the AC signal generator comprises a first signal source operatively connected to the first pair of electrodes and a second signal source operatively connected to the second pair of electrodes.

6. The apparatus of claim 1, wherein the first AC signal and the second AC signal are turned on at a rate that is slow relative to the reciprocal of the field frequency, and fast relative to the duration of the first output state.

7. The apparatus of claim 1, wherein the first AC signal and the second AC signal are turned on at a rate that reaches 90% of the steady-state values between 1-5 ms.

8. The apparatus of claim 1, wherein the periodic control signal is a square wave.

9. The apparatus of claim 2, wherein the AC signal generator comprises a single signal source and a switch that distributes an output of the single signal source to either the first pair of electrodes or the second pair of electrodes.

10. The apparatus of claim 2, wherein the AC signal generator comprises a first signal source operatively connected to the first pair of electrodes and a second signal source operatively connected to the second pair of electrodes.

11. The apparatus of claim 2, wherein the first AC signal and the second AC signal are turned on at a rate that is slow relative to the reciprocal of the field frequency, and fast relative to the duration of the first output state.

12. The apparatus of claim 2, wherein the first AC signal and the second AC signal are turned on at a rate that reaches 90% of the steady-state values between 1-5 ms.

13. The apparatus of claim 2, wherein the periodic control signal is a square wave.

* * * * *